(12) United States Patent
Cronin et al.

(10) Patent No.: US 7,368,269 B1
(45) Date of Patent: May 6, 2008

(54) CRYSTALLIZATION OF MAPK/ERK KINASE 2

(75) Inventors: Ciaran N. Cronin, San Diego, CA (US); Douglas R. Dougan, Calgary (CA); Mark W. Knuth, El Cajon, CA (US); Michelle L. Kraus, Temecula, CA (US); Kheng Lim, San Diego, CA (US); Clifford D. Mol, San Diego, CA (US); Gyorgy Snell, Richmond, CA (US); Hua Zou, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 265 days.

(21) Appl. No.: 11/075,058

(22) Filed: Mar. 7, 2005

(51) Int. Cl.
*C12N 9/12* (2006.01)
*G01N 31/00* (2006.01)
*G06F 19/00* (2006.01)

(52) U.S. Cl. ............................. 435/194; 436/4; 702/27

(58) Field of Classification Search ................. 435/194
See application file for complete search history.

(56) References Cited

FOREIGN PATENT DOCUMENTS

EP    1 321 518 A1    6/2003
WO   WO 03/054180 A1   7/2003

OTHER PUBLICATIONS

Giege et al. Crystallogenesis of Biological Macromolecules: Facts and Perspectives, Acta Cryst. D., 1994, D50:339-350.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Appendix A—Sequence alignment of amino acids 61-388 of SEQ ID No. 1 and amino acids 55-400 of SEQ ID No. 4 from Ohren et al. (WO 03/054180). No date.*

* cited by examiner

*Primary Examiner*—David J. Steadman
*Assistant Examiner*—Suzanne M. Noakes
(74) *Attorney, Agent, or Firm*—C. Amy Smith (57) ABSTRACT

Provided are crystals relating to human mitogen-activated protein kinase kinase2 (MAPKK2), also known as MAPK/ERK Kinase2 (MEK2) and its various uses.

11 Claims, 2 Drawing Sheets

FIGURE 1

Amino acid sequence for full-length human wild type MEK2 with residues 61-388 underlined [SEQ ID NO:1]

```
  1 MLARRKPVLP ALTINPTIAE GPSPTSEGAS EANLVDLQKK LEELELDEQQ KKRLEAFLTQ
 61 KAKVGELKDD DFERISELGA GNGGVVTKVQ HRPSGLIMAR KLIHLEIKPA IRNQIIRELQ
121 VLHECNSPYI VGFYGAFYSD GEISICMEHM DGGSLDQVLK EAKRIPEEIL GKVSIAVLRG
181 LAYLREKHQI MHRDVKPSNI LVNSRGEIKL CDFGVSGQLI DSMANSFVGT RSYMAPERLQ
241 GTHYSVQSDI WSMGLSLVEL AVGRYPIPPP DAKELEAIFG RPVVDGEEGE PHSISPRPRP
301 PGRPVSGHGM DSRPAMAIFE LLDYIVNEPP PKLPNGVFTP DFQEFVNKCL IKNPAERADL
361 KMLTNHTFIK RSEVEEVDFA GWLCKTLRLN QPGTPTRTAV
```

DNA sequence encoding the amino acid sequence of SEQ ID NO:3 [SEQ ID NO:2]

```
   1 ATGTCGTACT ACCATCACCA TCACCATCAC GATTACGATA TCCCAACGAC CGAAAACCTG
  61 TATTTTCAGG GCGCCATGGG ATCCAAAGCC AAGGTCGGCG AACTCAAAGA CGATGACTTC
 121 GAAAGGATCT CAGAGCTGGG CGCGGGCAAC GGCGGGGTGG TCACCAAAGT CCAGCACAGA
 181 CCCTCGGGCC TCATCATGGC CAGGAAGCTG ATCCACCTTG AGATCAAGCC GGCCATCCGG
 241 AACCAGATCA TCCGCGAGCT GCAGGTCCTG CACGAATGCA ACTCGCCGTA CATCGTGGGC
 301 TTCTACGGGG CCTTCTACAG TGACGGGGAG ATCAGCATTT GCATGGAACA CATGGACGGC
 361 GGCTCCCTGG ACCAGGTGCT GAAAGAGGCC AAGAGGATTC CGAGGAGAT CCTGGGGAAA
 421 GTCAGCATCG CGGTTCTCCG GGGCTTGGCG TACCTCCGAG AGAAGCACCA GATCATGCAC
 481 CGAGATGTGA AGCCCTCCAA CATCCTCGTG AACTCTAGAG GGGAGATCAA GCTGTGTGAC
 541 TTCGGGGTGA GCGGCCAGCT CATAGACGAA ATGGCCAACG ACTTCGTGGG CACGCGCTCC
 601 TACATGGCTC CGGAGCGGTT GCAGGGCACA CATTACTCGG TGCAGTCGGA CATCTGGAGC
 661 ATGGGCCTGT CCCTGGTGGA GCTGGCCGTC GGAAGGTACC CCATCCCCCC GCCCGACGCC
 721 AAAGAGCTGG AGGCCATCTT TGGCCGGCCC GTGGTCGACG GGGAAGAAGG AGAGCCTCAC
 781 AGCATCTCGC CTCGGCCGAG GCCCCCCGGG CGCCCCGTCA GCGGTCACGG GATGGATAGC
 841 CGGCCTGCCA TGGCCATCTT TGAACTCCTG GACTATATTG TGAACGAGCC ACCTCCTAAG
 901 CTGCCCAACG GTGTGTTCAC CCCCGACTTC CAGGAGTTTG TCAATAAATG CCTCATCAAG
 961 AACCCAGCGG AGCGGGCGGA CCTGAAGATG CTCACAAACC ACACCTTCAT CAAGCGGTCC
1021 GAGGTGGAAG AAGTGGATTT TGCCGGCTGG TTGTGTAAAA CCCTGCGGTA G
```

Amino acid sequence for residues 61-388 of MEK2 with a N-terminal 6x-histidine tag, spacer region and rTEV cleavage site, and with Ser222 to Glu and Ser226 to Asp mutations underlined [SEQ ID NO:3]

```
  1 MSYYHHHHHH DYDIPTTENL YFQGAMGSKA KVGELKDDDF ERISELGAGN GGVVTKVQHR
 61 PSGLIMARKL IHLEIKPAIR NQIIRELQVL HECNSPYIVG FYGAFYSDGE ISICMEHMDG
121 GSLDQVLKEA KRIPEEILGK VSIAVLRGLA YLREKHQIMH RDVKPSNILV NSRGEIKLCD
181 FGVSGQLIDE MANDFVGTRS YMAPERLQGT HYSVQSDIWS MGLSLVELAV GRYPIPPPDA
241 KELEAIFGRP VVDGEEGEPH SISPRPRPPG RPVSGHGMDS RPAMAIFELL DYIVNEPPPK
301 LPNGVFTPDF QEFVNKCLIK NPAERADLKM LTNHTFIKRS EVEEVDFAGW LCKTLR
```

FIGURE 2

CRYSTALLIZATION OF MAPK/ERK KINASE 2

FIELD OF THE INVENTION

The present invention relates to a member of a family of protein kinases and more specifically to Mitogen-Activated Protein Kinase Kinase 2 (MAPKK2), also known as MAPK/ERK Kinase 2 (MEK2). Provided are MEK2 in crystalline form, methods of forming crystals comprising MEK2, and methods of using crystals comprising MEK2.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein. A need thus exists for proteins in crystalline form.

SUMMARY OF THE INVENTION

The present invention is directed to crystals comprising MEK2 and particularly crystals comprising MEK2 that have sufficient size and quality to obtain useful information about the structural properties of MEK2 and molecules or complexes that may associate with MEK2.

In one embodiment, a composition is provided that comprises a protein in crystalline form wherein at least a portion of the protein has 55%, 65%, 75%, 85%, 90%, 95%, 97%, 99% or greater identity with residues 61-388 of SEQ ID NO:1.

In one variation, the protein has activity characteristic of MEK2. For example, the protein may optionally be inhibited by inhibitors of wild type MEK2. The protein crystal may also diffract X-rays for a determination of structure coordinates to a resolution of 4 Å, 3.5 Å, 3.0 Å, 2.5 Å or less.

In one variation, the protein crystal has a crystal lattice in a P2$_1$ space group. The protein crystal may also have a crystal lattice having unit cell dimensions, +/−5%, of a=58.028 Å, b=43.442 Å, c=135.778 Å, α=90.0°, β=102.13°, γ=90.0°.

The present invention is also directed to crystallizing MEK2. The present invention is also directed to the conditions useful for crystallizing MEK2. It should be recognized that a wide variety of crystallization methods can be used in combination with the crystallization conditions to form crystals comprising MEK2 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 61-388 of SEQ ID NO:1; and storing the crystallization volume under conditions suitable for crystal formation.

In one variation, the crystallization volume comprises equal volumes of the protein at 19.1 mg/ml in 25 mM Tris pH 7.6, 250 mM NaCl, 0.25 mM TCEP, 0.1 mM EDTA, and the precipitant solution comprising 24% PEG 4000; 20% glycerol, 0.16 M MgCl$_2$ and 0.08M Tris buffer pH=8.5, at 20° C.

The method may optionally further comprise forming a protein crystal that has a crystal lattice in a P2$_1$ space group. The method also optionally further comprises forming a protein crystal that has a crystal lattice having unit cell dimensions, +/−5%, of a=58.028 Å, b=43.442 Å, c=135.778 Å, α=90.0°, β=102.13°, γ=90.0°. The invention also relates to protein crystals formed by these methods.

The present invention is also directed to a composition comprising an isolated protein that comprises or consists of one or more of the protein sequence(s) of MEK2 taught herein for crystallizing MEK2. The present invention is also directed to a composition comprising an isolated nucleic acid molecule that comprises or consists of the nucleotides for expressing the protein sequence of MEK2 taught herein for crystallizing MEK2.

The present invention is also directed to an expression vector that may be used to express the isolated proteins taught herein for crystallizing MEK2. In one variation, the expression vector comprises a promoter that promotes expression of the isolated protein.

The present invention is also directed to a cell line transformed or transfected by an isolated nucleic acid molecule or expression vector of the present invention.

In regard to each of these embodiments, the protein may optionally have activity characteristic of MEK2. For example, the protein may optionally be inhibited by inhibitors of wild type MEK2.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 61-388 of SEQ ID NO:1; and performing rational drug design using a three dimensional structure that is based on the obtained structure coordinates.

The protein crystals may optionally have a crystal lattice with a P2$_1$ space group and unit cell dimensions, +/−5%, of a=58.028 Å, b=43.442 Å, c=135.778 Å, α=90.0°, β=102.13°, γ=90.0°.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. SEQ ID NOs:1, 2, and 3 referred to in this application.

DETAILED DESCRIPTION OF THE INVENTION

The present invention relates to a member of a family of protein kinases and more specifically to a particular kinase known as MAP/ERK Kinase2 (MEK2). Provided is MEK2 in crystalline form, and methods of forming crystals comprising MEK2.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

It will be readily apparent to those of skill in the art that the numbering of amino acids in other isoforms of MEK2 may be different than that set forth for MEK2. Corresponding amino acids in other isoforms of MEK2 are easily identified by visual inspection of the amino acid sequences or by using commercially available homology software programs, as further described below.

1. MEK2

The mitogen-activated protein kinase (MAPK) pathways are evolutionarily conserved from yeast to man and respond to a variety of extracellular signals to induce cell differentiation and proliferation. The extracellular-regulated kinase (ERK) cascade is one of three major MAPK signaling pathways and is the predominant cascade that controls cell proliferation, migration, division, and differentiation (Schaeffer, H. J., and Weber, M. J. (1999) Mol. Cell. Biol. 19, 2435-2444). In this pathway, binding of GTP to the Ras protein initiates a three protein kinase cascade, which leads to ERK activation through the intervening protein kinases Raf-1 and MEK1/2. The MEK1/2 kinases are dual-specificity threonine/tyrosine kinases that activate the downstream ERK kinase by phosphorylating specific ERK threonine and tyrosine residues, and are themselves activated by phosphorylation of MEK serine residues by the upstream RAF kinase. MEK1 and MEK2 share a high degree of amino acid sequence similarity, particularly in their kinase domains, and both are capable of phosphorylating ERK (Zheng, C-F., and Guan, K. (1993) J. Biol. Chem. 268, 11435-11439).

Multiple studies have linked the RAF/MEK/ERK signaling pathway to the growth and survival of many diverse human tumors including, but not limited to cancers of the colon, pancreas ovaries, and non-small-cell lung cancers (reviewed in: Sebolt-Leopold, J. S. and Herrera R. (2004) Nature Reviews: Cancer, 4, 937-947). For these reasons there has been considerable interest in developing small molecule pharmaceutical inhibitors of this pathway. These include the RAF kinase inhibitor BAY 43-9006, currently in Phase III clinical testing, and which possesses an IC50 of 12 nM against recombinant RAF kinase with in vivo activity against colon, pancreas an ovarian tumor models (Lee, J. T and McCubrey, J. A. (2003) Curr. Opin. Invest. Drugs. 4, 757-763). The X-ray co-crystal structure of BAY 43-9006 bound to B-RAF kinase shows that the inhibitor targets an inactive conformation of the enzyme (Wan, P. T., Garnett M. J., Roe S. M., Lee S., Niculescu-Duvaz D., Good V. M., Jones C. M., Marshall C. J., Springer C. J., Barford D., Marais R.; Cancer Genome Project (2004) Cell, 116, 855-867). Several non-ATP competitive MEK inhibitors have also entered clinical trials with the most advanced being CI-1040, which was shown to be metabolically unstable and further development was terminated during Phase II trials (Sebolt-Leopold, J. S. and Herrera R. (2004) Nature Reviews Cancer, 4, 937-947). Recent co-crystal structures of MEK1 and MEK2 show the structural basis for their inhibition by the CI-1040 class of compounds, which induce a conformational change in the kinase activation loop and shifts the control, or C-, helix such that the enzyme is trapped in a closed and catalytically inactive conformation (Ohren J. F., Chen H., Pavlovsky A., Whitehead C., Zhang E., Kuffa P., Yan C., McConnell P., Spessard C., Banotai C., Mueller W. T., Delaney A., Omer C., Sebolt-Leopold J., Dudley D. T., Leung I. K., Flamme C., Warmus J., Kaufman M., Barrett S., Tecle H., Hasemann C. A. (2004) Nat. Struct. Mol. Biol. 11, 1192-1197). The activating Ser222→Glu and Ser226→Asp site-directed mutations introduced into the current MEK2 construct allows the construct to be grown both with or without ATP present, and in the absence of any non-ATP competitive inhibitors. Accordingly, the construct is believed to relate to the biologically-relevant active kinase conformation, and is thus directly pertinent to inhibitor binding and the design of new ATP-competitive MEK inhibitors.

In one embodiment, MEK2 comprises the wild-type form of full length MEK2, set forth herein as SEQ. SEQ ID NO:1 (GenBank Accession Number NM_030662; (C.-F. Zheng & K. Guan, J. Biol. Chem., 268, 11435-11439 (1993)).

In another embodiment, MEK2 comprises residues 61-388 of SEQ ID NO:1 which comprises the active site domain of wild-type MEK2. The "active site binding pockets" or "active site" of MEK2 refers to the area on the surface of MEK2 where the substrate binds.

It should be recognized that the invention may be readily extended to various variants of wild-type MEK2 and variants of fragments thereof. In another embodiment, MEK2 comprises a sequence wherein at least a portion of the sequence has 55%, 65%, 75%, 85%, 90%, 95%, 97%, 99% or greater identity with SEQ ID NO:1.

It is also noted that the above sequences of MEK2 are also intended to encompass isoforms, mutants and fusion proteins of these sequences. An example of a fusion protein is provided by SEQ ID NO:3, which includes a 6 residue N-terminal tag (6 residues are histidine) and a rTEV protease cleavage site that may be used to facilitate purification of the protein.

A wide variety of MEK2 variants (e.g., insertions, deletions, substitutions, etc.) that fall within the above specified identity ranges may be designed and manufactured utilizing recombinant DNA techniques well known to those skilled in the art. These modifications can be used in a number of combinations to produce the variants. The present invention is useful for crystallizing and then solving the structure of the range of variants of MEK2.

Variants of MEK2 may be insertional variants in which one or more amino acid residues are introduced into a predetermined site in the MEK2 sequence. For instance, insertional variants can be fusions of heterologous proteins or polypeptides to the amino or carboxyl terminus of the subunits.

Variants of MEK2 also may be substitutional variants in which at least one residue has been removed and a different residue inserted in its place. Non-natural amino acids (i.e., amino acids not normally found in native proteins), as well as isosteric analogs (amino acid or otherwise), may optionally be employed in substitutional variants. Examples of suitable substitutions are well known in the art, such as Glu→Asp, Asp→Glu, Ser→Cys, and Cys→Ser for example. In the case of MEK2, phosphomimetic mutants have been engineered for the two serine residues (Ser222→Glu, Ser226→Asp) that are phosphorylated by the upstream RAF kinase to activate MEK2 kinase activity [SEQ ID NO:3].

Another class of variants is deletional variants, which are characterized by the removal of one or more amino acid residues from the MEK2 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution with bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding MEK2 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for their affect on a variety of different properties including, for example, solubility, crystallizability and a modification to the protein's structure and activity.

In one variation, the variant and/or fragment of wild-type MEK2 is functional in the sense that the resulting protein is capable of associating with at least one same chemical entity that is also capable of selectively associating with a protein comprising the wild-type MEK2 (e.g., residues 61-388 of SEQ. ID No. 1) since this common associative ability evidences that at least a portion of the native structure has been conserved.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of MEK2, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of MEK2 will depend, in part, on the region where the substitution, addition or deletion occurs in the crystal structure. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine; isoleucine; valine; glycine; alanine; asparagine; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of MEK2 will be apparent to those having skills in the art.

2. Cloning, Expression and Purification of MEK2

The gene encoding MEK2 can be isolated from RNA, cDNA or cDNA libraries. In this case, the portion of the gene encoding amino acid residues 61-388 (SEQ ID NO:1), corresponding to the kinase catalytic domains, was isolated and engineered to a DNA sequence shown as SEQ ID NO:2, which encodes the recombinant protein of SEQ ID NO:3.

Construction of expression vectors and recombinant proteins from the DNA sequence encoding MEK2 may be performed by various methods well known in the art. For example, these techniques may be performed according to Sambrook et al., Molecular Cloning—A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of MEK2. Example 1 provides one such expression system.

Once expressed, purification steps are employed to produce MEK2 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

MEK2 may optionally be affinity labeled during cloning, preferably with a N-terminal six-histidine tag and rTEV protease cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization and Crystals Comprising MEK2

One aspect of the present invention relates to methods for forming crystals comprising MEK2 as well as crystals comprising MEK2.

In one embodiment, a method for forming crystals comprising MEK2 is provided comprising forming a crystallization volume comprising MEK2, one or more precipitants, optionally a buffer, optionally a monovalent and/or divalent salt and optionally an organic solvent; and storing the crystallization volume under conditions suitable for crystal formation.

In yet another embodiment, a method for forming crystals comprising MEK2 is provided comprising forming a crystallization volume comprising MEK2 in solution comprising the components shown in Table 1; and storing the crystallization volume under conditions suitable for crystal formation.

TABLE 1

Precipitant 5-50% w/v of precipitant wherein the precipitant comprises one or more members of the group consisting of PEG having a molecular weight range between 1000-10000, or methoxy-PEG having a molecular weight range between 100-10000.

pH pH 4-10. Buffers that may be used include, but are not limited to tris, bicine, phosphate, cacodylate, acetate, citrate, HEPES, PIPES, MES and combinations thereof.

Additives

Optionally 0.05 to 2.5 M additives wherein the additives comprise a monovalent and/or divalent salt (for example, sodium, lithium, magnesium, calcium, and the like), and 0-50% w/v glycerol.

Protein Concentration 1 mg/ml-50 mg/ml

Temperature

1° C.-25° C.

In yet another embodiment, a method for forming crystals comprising MEK2 is provided comprising forming a crystallization volume comprising MEK2; introducing crystals comprising MEK2 as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising MEK2 and crystals comprising MEK2 according to the invention are not intended to be limited to the wild type, full length MEK2 shown in SEQ ID NO:1 and fragments comprising residues 61-388 of SEQ ID NO:1. Rather, it should be recognized that the invention may be extended to various other fragments and variants of wild-type MEK2 as described above.

It should also be understood that forming crystals comprising MEK2 and crystals comprising MEK2 according to the invention may be such that MEK2 is optionally complexed with one or more ligands and one or more copies of the same ligand. The ligand used to form the complex may be any ligand capable of binding to MEK2. In one variation, the ligand is a natural substrate. In another variation, the ligand is an inhibitor.

In one particular embodiment, MEK2 crystals have a crystal lattice in the $P2_1$ space group. MEK2 crystals may also optionally have unit cell dimensions, +/−5%, of a=58.028 Å, b=43.442 Å, c=135.778 Å, $\alpha$=90.0°, $\beta$=102.13°, $\gamma$=90.0°. MEK2 crystals also preferably are capable of diffracting X-rays for determination of atomic coordinates to a resolution of 4 Å, 3.5 Å, 3.0 Å or better.

Crystals comprising MEK2 may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, 2nd Ed. (1999), Academic Press Inc. Further descriptions regarding performing crystallization experiments are provided in Stevens et al. (2000) *Curr. Opin. Struct. Biol.*: 10(5):558-63, and U.S. Pat. Nos. 6,296,673; 5,419,278; and 5,096,676.

In one variation, crystals comprising MEK2 are formed by mixing substantially pure MEK2 with an aqueous buffer containing a precipitant at a concentration just below a concentration necessary to precipitate the protein. One suitable precipitant for crystallizing MEK2 is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a MEK2 complex were obtained. In order to accomplish this, systematic broad screen crystallization trials were performed on an MEK2 complex using the sitting drop technique. In each experiment, a 100 mL mixture of MEK2 complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Figure 2:
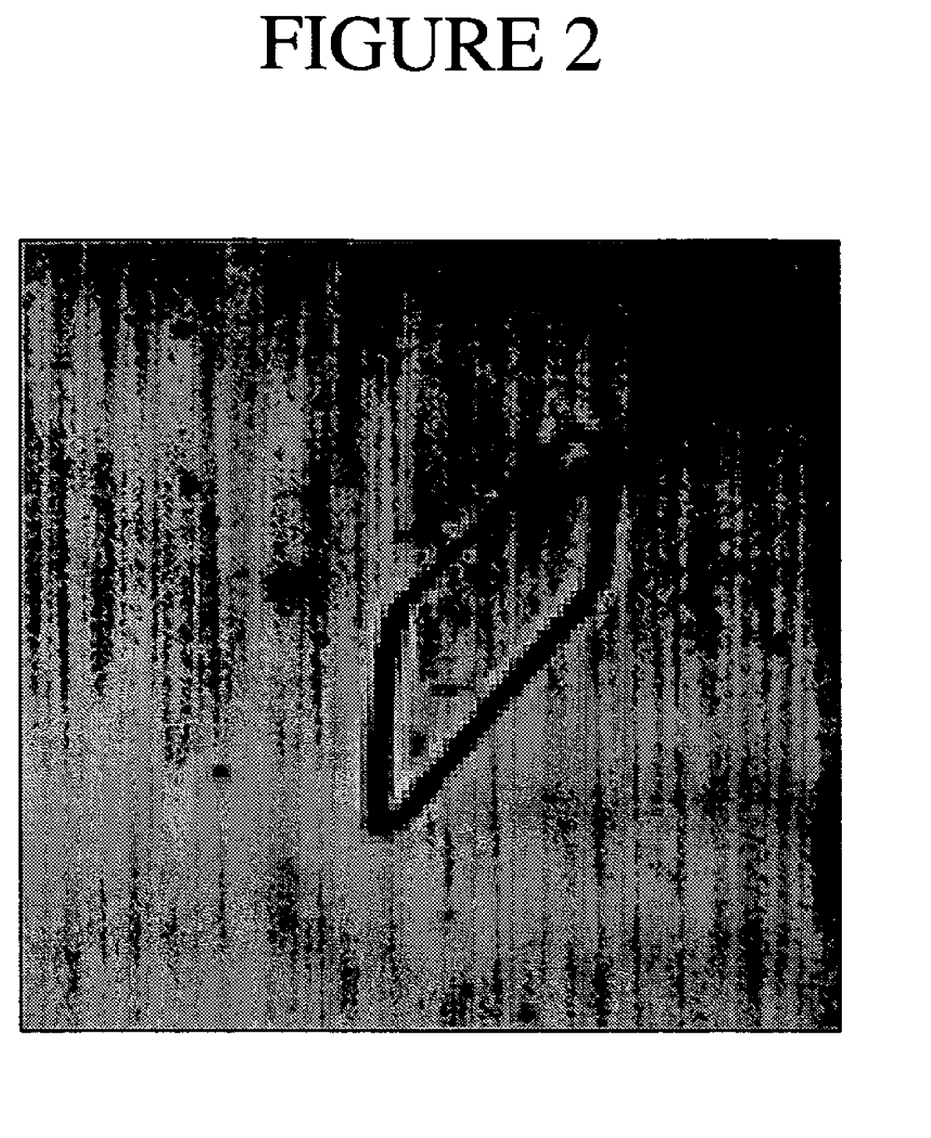
FIG. 2 illustrates a crystal of MEK2 corresponding to SEQ ID NO:3, having a crystal lattice in a P2$_1$ space group and unit cell dimensions, +/−5%, of a=58.028 Å, b=43.442 Å, c=135.778 Å, α=90.0°, β=102.13°, γ=90.0°.

Based on the crystallization experiments that were performed, a thorough understanding of how different crystallization conditions affect MEK2 crystallization was obtained. Based on this understanding, a series of crystallization conditions were identified that may be used to form crystals comprising MEK2. These conditions are summarized in Table 1. A particular example of crystallization conditions that may be used to form diffraction quality crystals of the MEK2 complex is detailed in Example 2. FIG. 2 illustrates crystals of the MEK2 complex formed using the crystallization conditions provided in Table 1.

One skilled in the art will recognize that the crystallization conditions provided in Table 1 and Example 2 can be varied and still yield protein crystals comprising MEK2. For example, it is noted that variations on the crystallization conditions described herein can be readily determined by taking the conditions provided in Table 1 and performing fine screens around those conditions by varying the type and concentration of the components in order to determine additional suitable conditions for crystallizing MEK2, variants of MEK2, and ligand complexes thereof.

Crystals comprising MEK2 have a wide range of uses. For example, now that crystals comprising MEK2 have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising MEK2 according to the present invention, the crystals so formed can be used by this crystallization technique to initiate crystal growth of other MEK2 comprising crystals, including MEK2 complexed to other ligands.

As will be described herein in greater detail, crystals may also be used to perform X-ray or neutron diffraction analysis in order to determine the three-dimensional structure of MEK2 and, in particular, to assist in the identification of its active site. Knowledge of the binding site region allows rational design and construction of ligands including inhibitors.

Crystallization and structural determination of MEK2 mutants having altered bioactivity allows the evaluation of whether such changes are caused by general structure deformation or by side chain alterations at the substitution site.

4. X-Ray Data Collection and Structure Determination

Crystals comprising MEK2 may be obtained as described above in Section 3. As described herein, these crystals may then be used to perform X-ray data collection and for structure determination.

In one embodiment, described in Example 2, crystals of MEK2 were obtained where MEK2 has the sequence of residues shown in SEQ ID NO:3. However, it is noted that other crystals comprising MEK2 including different MEK2 variants, fragments, and complexes thereof may also be used.

Diffraction data were collected from cryocooled crystals (100K) of MEK2 at the Advanced Light Source (ALS) beam line 5.0.3 using an ADSC Quantum CCD detector. The diffraction pattern of the MEK2 crystals displayed symmetry consistent with space group P2, with unit cell dimensions a=58.028 Å, b=43.442 Å, c=135.778 Å, $\alpha$=90.0°, $\beta$=102.13°, $\gamma$=90.0° (+/−5%). Data were collected and integrated to 2.9 Å with the HKL2000 program package (Otwinowski, Z. and Minor, W., *Meth. Enzymol.* 276:307 (1997)).

The X-ray diffraction data collection statistics are given in Table 2.

TABLE 2

| Crystal data | |
|---|---|
| Space group | P2$_1$ |
| Unit cell dimensions | a = 58.028Å |
| | b = 43.442Å |
| | c = 135.778Å |
| | $\alpha$ = 90.0° |
| | $\beta$ = 102.13° |
| | $\gamma$ = 90.0° |

| Data collection | | |
|---|---|---|
| X-ray source | | ALS BL 5.0.3 |
| Wavelength [Å] | | 1.00 |
| Resolution [Å] | | 1.85Å |
| Observations (unique) | | 56586 |
| Redundancy | | 3.2 |
| Completeness | overall (outer shell) | 99.1 (93.2) % |
| I/$\sigma$(I) | overall (outer shell) | 12.3 (1.8) |
| R$_{symm}$[1] | overall (outer shell) | 0.050 (.473) |

Based on crystal volume calculations, where the unit cell dimensions were a=58.028 Å, b=43.442 Å, c=135.778 Å, $\alpha$=90.0°, $\beta$=102.13°, $\gamma$=90.0°, it was realized that the asymmetric unit comprised two MEK2 molecules.

5. Uses of the Crystal and Diffraction Pattern of MEK2

Crystals, crystallization conditions and the diffraction pattern of MEK2 that can be generated from the crystals also have a range of uses. One particular use relates to screening entities that are not known ligands of MEK2 for their ability to bind to MEK2. For example, with the availability of crystallization conditions, crystals and diffraction patterns of MEK2 provided according to the present invention, it is possible to take a crystal of MEK2; expose the crystal to one or more entities that may be a ligand of MEK2; and determine whether a ligand/MEK2 complex is formed. The crystals of MEK2 may be exposed to potential ligands by various methods, including but not limited to, soaking a crystal in a solution of one or more potential ligands or co-crystallizing MEK2 in the presence of one or more potential ligands.

Once one or more ligands are identified, structural information from the ligand/MEK2 complex(es) may be used to design new ligands that bind tighter, bind more specifically, have better biological activity or have better safety profiles than known ligands.

In one embodiment, a method is provided for identifying a ligand that binds to MEK2 comprising: (a) attempting to crystallize a protein that comprises a sequence wherein at least a portion of the sequence has 55%, 65%, 75%, 85%, 90%, 95%, 97%, 99% or greater identity with SEQ ID NO:3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to MEK2 comprising: soaking a crystal of a protein wherein at least a portion of the protein has 55%, 65%, 75%, 85%, 90%, 95%, 97%, 99% or greater identity with SEQ ID NO:3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-MEK2 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

According to another embodiment, the invention provides compounds that associate with an MEK2-like binding pocket produced or identified by various methods set forth above. The terms "binding site" or "binding pocket", as used herein, refer to a region of a protein that, as a result of its shape, favorably associates with a ligand or substrate. Similarly, the term "MEK2-like binding pocket" refers to a portion of a molecule or molecular complex whose shape is sufficiently similar to the MEK2 binding pockets as to bind common ligands. This commonality of shape may be quantitatively defined based on a comparison to a reference point (e.g., a set of structure coordinates). For example, the commonality of shape may be quantitatively defined based on a root mean square deviation (RMSD) from the structure coordinates of the backbone atoms of the amino acids that make up the binding pockets in MEK2).

EXAMPLES

Example 1

Expression and Purification of MEK2

This example describes cloning, expression and purification of MEK2. It should be noted that a variety of other expression systems and hosts are also suitable for the expression of MEK2, as would be readily appreciated by one of skill in the art.

The portion of the gene encoding residues 61-388 (from SEQ ID NO:1), which corresponds to the catalytic domain of human MEK2, was cloned into a modified pFastBacHTc vector (also known as pSXB1) at the BamHI and XbaI sites. Expression from this vector produced the recombinant MEK2 catalytic domain with a 6x-histidine tag at the N-terminus followed by a rTEV protease cleavage sequence to facilitate tag removal (the 6x-Histidine tag and rTEV cleavage site sequences are underlined in SEQ ID NO:2). Recombinant baculovirus genomic DNAs incorporating the MEK2 catalytic domain cDNA sequences were generated by transposition using the Bac-to-Bac system (Invitrogen). Infectious viral particles were obtained by transfection of a 2 ml adherent culture of *Spodoptera frugiperda* Sf9 insect cells with the recombinant viral genomic DNA. Growth in ESF 921 protein free medium (Expression Systems) was for 3 days at 27° C. The resulting Passage 0 viral supernatant was used to obtain Passage 1 high titer viral stock (HTS) by infection of a 30 ml adherent culture of *Spodoptera frugiperda* Sf9 insect cells grown under similar conditions. Passage 1 HTS was used in turn to infect a 100 ml suspension culture of *Spodoptera frugiperda* Sf9 insect cells in order to generate Passage 2 HTS.

Passage 2 HTS was used to infect a 5-liter culture of *Spodoptera frugiperda* Sf9 insect cells (at a density of approx. $3\times10^6$ cells/ml) in a 10 liter Wave BioReactor grown in ESF-921 serum-free medium at a multiplicity of infection (moi) of approximately 5 (empirical value based on usual HTS viral counts). Cell growth/infection proceeded for two days after which time the cells were pelleted by centrifugation and the cell pellet stored at −80° C. until required. Frozen cell pellets from two such 5-liter cultures were removed from the −80° C. freezer and each suspended in 150 ml of Lysis Buffer (50 mM Tris-HCl, pH 7.9, 200 mM NaCl, 0.25 mM TCEP, 1 mM PMSF and 2 'Complete-EDTA' Roche Protease Inhibitor tablets). The suspensions were stirred for 45 min at 4° C. followed by centrifugation at 7,000 g for 1 h. To each supernatant were added 8 ml of a 50% slurry of ProBond (InVitrogen) resin that had been equilibrated in Lysis Buffer without protease inhibitors. The suspensions were mixed for 90 min followed by centrifugation at 640 g for 5 min. The supernatants were discarded and the resin pellets washed three times with 50 mM potassium phosphate, pH 7.9, 400 mM NaCl, 0.25 mM TCEP and 1 µg/mL leupeptin. Each resin sample was transferred to an Omnifit chromatography column (10 cm×1.5 cm diameter) at 4° C. and washed with 50 column volumes of 50 mM potassium phosphate, pH 7.9, 400 mM NaCl, 20 mM imidazole-HCl, pH 7.9, 0.25 mM TCEP and 1 µg/mL leupeptin. The columns were subsequently washed with 5 column volumes of 50 mM Tris-HCl, pH 7.9, 400 mM NaCl, 0.25 mM TCEP and 1 µg/mL leupeptin. Target elution was effected by the addition of 50 mM Tris-HCl, pH 7.9, 400 mM NaCl, 200 mM imidazole-HCl, pH 7.9, 0.25 mM TCEP, 1 µg/mL leupeptin. Following three five-fold dilution buffer-exchanges into 25 mM Tris pH 7.6, 250 mM NaCl, 0.25 mM TCEP, 0.1 mM EDTA, MEK2 was further purified by size-exclusion chromatography on a Phenomenex BioSep-SEC-S 3000 chromatography column (30 cm×2.12 cm diameter). The purified MEK2 protein was concentrated to 19.1 mg/ml with a total volume of 0.87 ml (16.6 mg purified MEK2). The purified protein had the correct molecular mass (39,989) as determined by Mass Spectrograph (MS) analysis, was monomeric by analytical size-exclusion chromatography (SEC) and exhibited a major band by sodium-dodecyl-sulfate polyacrylamide gel electrophoresis (SDS-PAGE) analyses.

Example 2

Crystallization of MEK2

This example describes the crystallization of MEK2. It is noted that the precise crystallization conditions used may be further varied, for example by performing a fine screen based on these crystallization conditions.

MEK2 protein samples (corresponding to SEQ ID NO:3) were either run without addition of ligands or also incubated with 2.5 mM ATP and 5 mM $MgCl_2$ before setting up crystallization trials. Crystals were obtained after an extensive and broad screen of conditions, followed by optimization. Diffraction quality crystals were grown in 100 nl sitting droplets using the vapor diffusion method. 50 nl comprising a solution of MEK2 or the MEK2-ATP complex (19.1 mg/ml) was mixed with 50 nl from a reservoir solution (1001) comprising: 24% PEG 4000; 20% glycerol, 0.16 M $MgCl_2$ and 0.08M Tris buffer pH=8.5, at 20° C. These crystals could also be obtained from larger 2 µl droplets set up by hand using 1 µl of protein solution and 1 µl of reservoir solution. Crystals typically appeared after 3-5 days and grew to a maximum size within 7-10 days. Single crystals were harvested, flash frozen by immersion in liquid nitrogen, and then stored under liquid nitrogen. A crystal of MEK2 produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, patent applications, papers, and books cited in this application are incorporated herein in their entirety.

We claim:

1. A composition comprising a protein in crystalline form wherein the protein consists of SEQ ID NO:3, and wherein the protein crystal has a crystal lattice in a P2$_1$ space group and unit cell dimensions, +/−5%, of a=58.028 Å, b=43.442 Å, c=135.778 Å, α=90.0°, β=102.13°, γ=90.0°.

2. A composition according to claim 1 wherein the protein crystal diffracts X-rays for a determination of structure coordinates to a higher resolution than 3.0 Angstroms.

3. A composition according to claim 1 wherein the protein crystal diffracts X-rays for a determination of structure coordinates to a higher resolution than 2.5 Angstroms.

4. A composition comprising an isolated non-crystalline protein consisting of SEQ ID NO:3.

5. A composition comprising an isolated non-crystalline protein of claim 4, wherein the protein is encoded by a nucleic acid molecule that consists of SEQ ID NO:2.

6. A method for forming a crystal of a protein comprising:
forming a crystallization volume comprising a precipitant solution and a protein that consists of SEQ ID NO:3, and
storing the crystallization volume under conditions suitable for crystal formation until a protein crystal is formed, wherein the protein crystal has a crystal lattice in a P2$_1$ space group and unit cell dimensions, +/−5%, of a=58.028 Å, b=43.442 Å, c=135.778 Å, α=90.0°, β=102.13°, γ=90.0°.

7. The method according to claim 6 wherein the protein crystal diffracts X-rays for a determination of structure coordinates to a higher resolution than 3.0 Angstroms.

8. The method according to claim 6 wherein the protein crystal diffracts X-rays for a determination of structure coordinates to a higher resolution than 2.5 Angstroms.

9. A method according to claim 6, the method further comprising diffracting the protein crystal to produce a diffraction pattern.

10. The composition comprising a protein in crystalline form of claim 1, wherein SEQ ID No: 3 is encoded by the nucleic acid of SEQ ID No: 2.

11. A non crystalline, isolated protein consisting of SEQ ID NO:3.

* * * * *

SEQUENCE LISTING

```
<160> NUMBER OF SEQ ID NOS: 3

<210> SEQ ID NO 1
<211> LENGTH: 400
<212> TYPE: PRT
<213> ORGANISM: Homo Sapien
<220> FEATURE:
<221> NAME/KEY: MISC_FEATURE
<222> LOCATION: (61)..(388)
<223> OTHER INFORMATION: Amino acid sequence for residues 61-338 of
      full-length human wild type MEK2

<400> SEQUENCE: 1

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125
```

```
Tyr Ile Val Gly Phe Tyr Gly Ala Phe Tyr Ser Asp Gly Glu Ile Ser
        130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Lys Leu Pro Asn Gly
                325                 330                 335

Val Phe Thr Pro Asp Phe Gln Asp Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400

<210> SEQ ID NO 2
<211> LENGTH: 1071
<212> TYPE: DNA
<213> ORGANISM: Artificial
<220> FEATURE:
<223> OTHER INFORMATION: Artificial Sequence: DNA sequence encoding the
      amino acid sequence of SEQ ID NO. 3

<400> SEQUENCE: 2
atgtcgtact accatcacca tcaccatcac gattacgata tcccaacgac cgaaaacctg      60
tattttcagg gcgccatggg atccaaagcc aaggtcggcg aactcaaaga cgatgacttc     120
gaaaggatct cagagctggg cgcgggcaac ggcggggtgg tcaccaaagt ccagcacaga     180
ccctcgggcc tcatcatggc caggaagctg atccaccttg agatcaagcc ggccatccgg     240
aaccagatca tccgcgagct gcaggtcctg cacgaatgca actcgccgta catcgtgggc     300
ttctacgggg ccttctacag tgacggggag atcagcattt gcatggaaca catggacggc     360
ggctccctgg accaggtgct gaaagaggcc aagaggattc ccgaggagat cctggggaaa     420
gtcagcatcg cggttctccg gggcttggcg tacctccgag agaagcacca gatcatgcac     480
cgagatgtga agccctccaa catcctcgtg aactctagag gggagatcaa gctgtgtgac     540
```

```
ttcggggtga gcggccagct catagacgaa atggccaacg acttcgtggg cacgcgctcc    600
tacatggctc cggagcggtt gcagggcaca cattactcgg tgcagtcgga catctggagc    660
atgggcctgt ccctggtgga gctggccgtc ggaaggtacc ccatcccccc gcccgacgcc    720
aaagagctgg aggccatctt tggccggccc gtggtcgacg gggaagaagg agagcctcac    780
agcatctcgc ctcggccgag gccccccggg cgccccgtca gcggtcacgg gatggatagc    840
cggcctgcca tggccatctt tgaactcctg gactatattg tgaacgagcc acctcctaag    900
ctgcccaacg tgtgttcac ccccgacttc caggagtttg tcaataaatg cctcatcaag    960
aacccagcgg agcgggcgga cctgaagatg ctcacaaacc acaccttcat caagcggtcc   1020
gaggtggaag aagtggattt tgccggctgg ttgtgtaaaa ccctgcggta g            1071
```

<210> SEQ ID NO 3
<211> LENGTH: 376
<212> TYPE: PRT
<213> ORGANISM: Artificial
<220> FEATURE:
<223> OTHER INFORMATION: Artificial Sequence: Amino acid sequence for residues 61-388 of MEK2 with a N-terminal 6x-histidine tag, spacer region and rTEV cleavage site, and with Ser222 to Glu and Ser226 to Asp mutations

<400> SEQUENCE: 3

```
Met Ser Tyr Tyr His His His His His His Asp Tyr Asp Ile Pro Thr
 1               5                  10                  15
Thr Glu Asn Leu Tyr Phe Gln Gly Ala Met Gly Ser Lys Ala Lys Val
                20                  25                  30
Gly Glu Leu Lys Asp Asp Asp Phe Glu Arg Ile Ser Glu Leu Gly Ala
             35                  40                  45
Gly Asn Gly Gly Val Val Thr Lys Val Gln His Arg Pro Ser Gly Leu
         50                  55                  60
Ile Met Ala Arg Lys Leu Ile His Leu Glu Ile Lys Pro Ala Ile Arg
 65                  70                  75                  80
Asn Gln Ile Ile Arg Glu Leu Gln Val Leu His Glu Cys Asn Ser Pro
                 85                  90                  95
Tyr Ile Val Gly Phe Tyr Gly Ala Phe Tyr Ser Asp Gly Glu Ile Ser
            100                 105                 110
Ile Cys Met Glu His Met Asp Gly Gly Ser Leu Asp Gln Val Leu Lys
        115                 120                 125
Glu Ala Lys Arg Ile Pro Glu Glu Ile Leu Gly Lys Val Ser Ile Ala
    130                 135                 140
Val Leu Arg Gly Leu Ala Tyr Leu Arg Glu Lys His Gln Ile Met His
145                 150                 155                 160
Arg Asp Val Lys Pro Ser Asn Ile Leu Val Asn Ser Arg Gly Glu Ile
                165                 170                 175
Lys Leu Cys Asp Phe Gly Val Ser Gly Gln Leu Ile Asp Glu Met Ala
            180                 185                 190
Asn Asp Phe Val Gly Thr Arg Ser Tyr Met Ala Pro Glu Arg Leu Gln
        195                 200                 205
Gly Thr His Tyr Ser Val Gln Ser Asp Ile Trp Ser Met Gly Leu Ser
    210                 215                 220
Leu Val Glu Leu Ala Val Gly Arg Tyr Pro Ile Pro Pro Pro Asp Ala
225                 230                 235                 240
Lys Glu Leu Glu Ala Ile Phe Gly Arg Pro Val Val Asp Gly Glu Glu
                245                 250                 255
```

-continued

```
Gly Glu Pro His Ser Ile Ser Pro Arg Pro Arg Pro Gly Arg Pro
            260             265             270

Val Ser Gly His Gly Met Asp Ser Arg Pro Ala Met Ala Ile Phe Glu
        275             280             285

Leu Leu Asp Tyr Ile Val Asn Glu Pro Pro Lys Leu Pro Asn Gly
    290             295             300

Val Phe Thr Pro Asp Phe Gln Glu Phe Val Asn Lys Cys Leu Ile Lys
305             310             315             320

Asn Pro Ala Glu Arg Ala Asp Leu Lys Met Leu Thr Asn His Thr Phe
            325             330             335

Ile Lys Arg Ser Glu Val Glu Glu Val Asp Phe Ala Gly Trp Leu Cys
            340             345             350

Lys Thr Leu Arg Ala Asn Asn Thr Ala Thr Glu Asp Asp Arg Ala Trp
        355             360             365

Ile Asn Gly Ser His Glu Glu Thr
    370             375
```